United States Patent [19]

Burkhart et al.

[11] Patent Number: 5,606,067
[45] Date of Patent: Feb. 25, 1997

[54] PREPARATION OF N-ALLYL COMPOUNDS

[75] Inventors: Bernd Burkhart, Mutterstadt; Alfred Oftring, Bad Durkheim; Rudi Widder, Leimen; Ulrich Schroeder, Frankenthal, all of Germany

[73] Assignee: BASF Aktiengesellschaft, Ludwigshafen, Germany

[21] Appl. No.: 318,743

[22] PCT Filed: May 5, 1993

[86] PCT No.: PCT/EP93/01090

§ 371 Date: Oct. 19, 1994

§ 102(e) Date: Oct. 19, 1994

[87] PCT Pub. No.: WO93/23377

PCT Pub. Date: Nov. 25, 1993

[30] Foreign Application Priority Data

May 16, 1992 [DE] Germany .................. 42 16 314.5

[51] Int. Cl.⁶ .................. C07D 213/127; C07D 213/20
[52] U.S. Cl. .................................................. 546/347
[58] Field of Search .............................. 546/347

[56] References Cited

PUBLICATIONS

Hendrickson, Organic Chemistry, Third Edition, 1970, pp. 9–10 1970.
Y. Kawazoe, *Chem Pharm Bull*, vol 30(6), pp. 2077–2086, 1982.
W. Gessner, *J Med Chem*, vol. 28, pp. 311–317, 1985.
J. Jaen, *J Med Chem*, vol. 33, pp. 311–317, 1990.
"Japanese Patent Publication", Sumitomo Chemical Co. Ltd., JA 7139690 equivalent to 015662 (28.2.69), pp. B3–E13.

*Primary Examiner*—C. Warren Ivy
*Assistant Examiner*—D. Margaret M. Mach
*Attorney, Agent, or Firm*—Oblon, Spivak, McClelland, Maier & Neustadt, P.C.

[57] ABSTRACT

A process for the preparation of N-allyl compounds of the general formula I

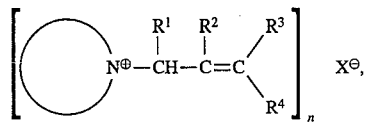

in which

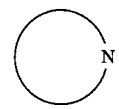

denotes a nitrogen-containing heterocyclic compound,
$R^1$, $R^3$, and $R^4$ independently denote hydrogen or $C_1$–$C_4$ alkyl,
$R^2$ denotes hydrogen or methyl,
n is equal to 1, 2, 3, or 4, and
X denotes a water-solubilizing anion,
wherein a compound of formula II

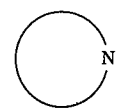

is caused to react, in aqueous medium, with a compound of formula III

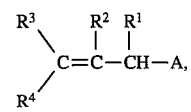

in which A denotes a radical which can be eliminated as an anion.

The compounds produced by the process of the invention are very well suited for use as brighteners in nickel electroplating.

8 Claims, No Drawings

PREPARATION OF N-ALLYL COMPOUNDS

This application is a 371 of PCT/EP93/01090, filed May 5, 1993.

DESCRIPTION

U.S. Pat. No. 4,029,658 has already described a process for the preparation of allylpyridinium chloride, in which pyridine is caused to react with allyl chloride in dimethylformamide.

Furthermore, the Japanese Patent Publication 62000447 describes the reaction of allyl chloride with pyridine in an autoclave.

The reaction of pyridine derivatives with crotyl bromide in benzene and acetone is described in the Japanese Patent Publication 7139690.

N-Allyl compounds and particularly those of pyridine containing water-soluble anions are usually hygroscopic and therefore show a pronounced tendency to become lumpy, which makes them difficult to employ in industrial processes. There has therefore been the desire to make such compounds available in a form which is easy to handle.

We have now found, surprisingly, that aqueous solutions comprise such a form and that such aqueous solutions can be prepared in a simple and economical manner.

Thus the present invention relates to the manufacturing process defined in claim 1.

Heterocyclics which can be caused to react with compounds of formula III in accordance with the present invention are, in particular, quinoline and isoquinoline compounds, which may in addition be substituted by $C_1$–$C_4$ alkyl, preferably pyridine optionally carrying alkyl radicals, and more preferably pyridine itself.

Compounds of formula III are, in particular, α-, β-, and γ-methyallyl halides, of which the chlorides and bromide are preferred. Thus n in formula I is preferably equal to 1. It is of course possible to exchange the halide anions for other water-solubilizing anions by conventional methods.

The reaction proposed in the present invention is preferably carried out in a purely aqueous medium. However, it is of course possible to use water together with water-soluble solvents such as alcohols, glycols, tetrahydrofuran, amides, or ketones. It is also possible to add emulsifiers, particularly oil-in-water type emulsifiers.

It is further preferred to cause the compounds II and III to react in stoichiometric amounts, the order of addition being arbitrary. That is to say, either: one of the compounds of formula II and III can be added to an aqueous solution containing compound III or II respectively, or: both of the compounds II and III can be added to water.

It is advantageous to carry out the reaction at an elevated temperature, for example a temperature just below the boiling point of the reaction mixture. The concentrations used are such as to give 20–80% strength and preferably 50–80% strength solutions of the compounds of formula I.

In order to remove residues of unconverted compounds of the formulas II and III, the reaction may be followed by steam distillation or the passage of an inert gas through the reaction mixture. Examples of inert gases are nitrogen, $CO_2$, or even air. It is important to ensure that the pH is kept between 4 and 8 and preferably between 5 and 6. Control of the pH can be effected, for example, by adding caustic soda solution.

Details on the preparation and reaction parameters are given in the following examples, in which the parts and percentages are by weight unless otherwise stated.

The products of the process of the invention are suitable, for example, for use as brighteners in the preparation of nickel-plated shaped articles by galvanic deposition of nickel from aqueous/acid baths.

EXAMPLE 1

Preparation of pyridinium allyl chloride 466.58; of water are placed in the reactor. 229.58; (3 mol) of allyl chloride are added and the mixture is heated to 50° C. 237.0g (3 mol) of pyridine are then added dropwise over a period of one hour with vigorous stirring. Following a further eight hours at 50° C. the reaction mixture is subjected to steam distillation at 500 mbar/80° C. During the steam distillation the pH is kept at 5 by means of dilute NaOH. Distillation is continued until the content of pyridine in the bottoms is less than 0.1%. The yield is 90%.

EXAMPLE 2

Preparation of pyridinium/β-methallyl chloride

This compound was prepared in a yield of 87% from pyridine and β-methallyl chloride in a manner similar to that described in Example 1.

EXAMPLE 3

Preparation of pyridinium γ-methallyl chloride

This compound was prepared in a yield of 83% from pyridine and γ-methallyl chloride in a manner similar to that described in Example 1.

We claim:

1. A process for the preparation of N-allyl compounds of the general formula I

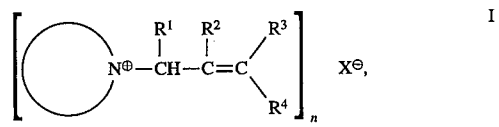

in which

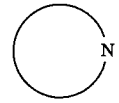

denotes a nitrogen-containing heterocyclic compound, $R^1$, $R^3$, and $R^4$ independently denote hydrogen or $C_1$–$C_4$-alkyl, $R^2$ denotes hydrogen or methyl, n is equal to 1, 2, 3, or 4, and $X^\ominus$ denotes a water-solubilizing anion, comprising the steps of:

a) contacting a compound of formula II

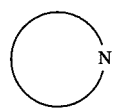

in aqueous medium, with a compound of formula III

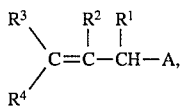

in which A denotes a radical which can be eliminated as an anion, and b) removing unconverted portions of compound II and/or compound III by effecting steam distillation or by passing an inert gas through the reaction mixture, during which procedures the pH is kept at a value between 4 and 8.

2. A process as defined in claim 1, wherein a compound is allylized in which

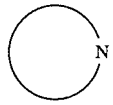

is derived from a pyridine, quinoline, or isoquinoline, which may in each case be substituted by $C_1$–$C_4$ alkyl.

3. A process as defined in claim 1, wherein the compound allylized is pyridine.

4. A process as defined in claim 1, wherein the compound of formula III used is an allyl halide or an α-, β-, or γ-methallyl halide.

5. A process as defined in claim 1, wherein $X^\ominus$ is a chloride or bromide.

6. A process as defined in claim 1, wherein the reaction is carried out optionally in the presence of an emulsifier and/or a water-soluble organic solvent.

7. A process as defined in claim 1, wherein the reaction is carried out using stoichiometric amounts of the compounds II and III.

8. A process as defined in claim 1, wherein unconverted portions of compound II and/or compound III are removed by effecting steam distillation or by passing an inert gas through the reaction mixture, during which procedures the pH is kept at a value between 5 and 6.

* * * * *